United States Patent
Tanaka et al.

(10) Patent No.: US 11,421,195 B2
(45) Date of Patent: Aug. 23, 2022

(54) CULTURE DEVICE

(71) Applicant: IHI CORPORATION, Tokyo (JP)

(72) Inventors: Hiroshi Tanaka, Tokyo (JP); Yoshiaki Matsuzawa, Tokyo (JP); Yuko Yoshida, Tokyo (JP); Norimitsu Kaneko, Tokyo (JP); Jun Muto, Tokyo (JP)

(73) Assignee: IHI CORPORATION, Tokyo (JP)

( * ) Notice: Subject to any disclaimer, the term of this patent is extended or adjusted under 35 U.S.C. 154(b) by 139 days.

(21) Appl. No.: 16/809,725

(22) Filed: Mar. 5, 2020

(65) Prior Publication Data

US 2020/0224141 A1    Jul. 16, 2020

Related U.S. Application Data

(63) Continuation of application No. PCT/JP2017/033753, filed on Sep. 19, 2017.

(51) Int. Cl.
*C12M 1/00* (2006.01)
*C12M 1/34* (2006.01)
*C12M 1/36* (2006.01)

(52) U.S. Cl.
CPC ............ *C12M 23/34* (2013.01); *C12M 29/06* (2013.01); *C12M 31/00* (2013.01); *C12M 41/36* (2013.01); *C12M 41/48* (2013.01)

(58) Field of Classification Search
None
See application file for complete search history.

(56) References Cited

U.S. PATENT DOCUMENTS

| 8,642,326 | B1 | 2/2014 | Schaefer et al. |
| 2010/0081122 | A1 | 4/2010 | Shibuya et al. |
| 2012/0036767 | A1 | 2/2012 | Larach |

(Continued)

FOREIGN PATENT DOCUMENTS

| CN | 104893952 B | 5/2017 |
| JP | S58-104610 A | 6/1983 |
| JP | H05-227943 A | 9/1993 |

(Continued)

OTHER PUBLICATIONS

Yoshiaki Matsuzawa, "Process Development for Production of Renewable Jet Fuel Using Hyper-Growth Botoryococcus braunii," Journal of the Japan Institute of Energy—Enermix, vol. 96, No. 1, pp. 34-39 (2017).

(Continued)

*Primary Examiner* — Liban M Hassan

(57) ABSTRACT

Provided is a culture device, including: a culture tank (110) configured to store an object liquid that is a culture solution having suspended therein an object; a screen (210) made of a metal, the screen including a main body (212) and a plurality of through holes (214) passing through the main body from a front surface (212a) thereof to a back surface (212b) thereof; a spray portion (220) configured to spray the object liquid stored in the culture tank onto the front surface of the body; an accommodation portion (240) surrounding the back surface of the main body and configured to accommodate the culture solution having passed through the through holes; a UV light irradiation portion (250) arranged in the accommodation portion and configured to radiate UV light; and a return portion (290) configured to return the culture solution in the accommodation portion to the culture tank.

8 Claims, 4 Drawing Sheets

(56) References Cited

U.S. PATENT DOCUMENTS

2018/0072984 A1  3/2018  Tanaka et al.

FOREIGN PATENT DOCUMENTS

| JP | H05-268935 | A | 10/1993 |
|----|-----------|---|---------|
| JP | H06-238110 | A | 8/1994 |
| JP | 2000-228975 | A | 8/2000 |
| JP | 2008-272761 | A | 11/2008 |
| JP | 2010-081809 | A | 4/2010 |
| JP | 2011-239746 | A | 12/2011 |
| JP | 2011-529707 | A | 12/2011 |
| JP | 4883067 | B2 | 2/2012 |
| JP | 2012-080850 | A | 4/2012 |
| JP | 2012-175964 | A | 9/2012 |
| JP | 2014-168415 | A | 9/2014 |
| JP | 2016-059867 | A | 4/2016 |
| JP | 2016-198715 | A | 12/2016 |
| JP | 2016-214151 | A | 12/2016 |
| JP | 2017-169517 | A | 9/2017 |
| WO | 2016/186174 | A1 | 11/2016 |

OTHER PUBLICATIONS

International Search Report received for PCT Patent Application No. PCT/JP2017/033753, dated Dec. 19, 2017, 4 pages (2 pages of English translation of International Search Report, and 2 pages of International Search Report).

European Patent Office, "Extended European Search Report," issued in European Patent Application No. 17 925 670.6, which is a counterpart to U.S. Appl. No. 16/809,725, dated Mar. 4, 2021, 32 pages.

Chatchadaporn Sananurak et al., "Development of a closed-recirculating, continuous culture system for microalga (*Tetraselmis suecica*) and rotifer (*Brachionus plicatilis*) production," ScienceAsia, vol. 35, pp. 118-124, 2009, DOI: 10.2306/scienceasial513-1874.2009.35.118.

Kuan-Yeow Show et al., "Algal biomass dehydration," Bioresource Technology, vol. 135, pp. 720-729, 2013, Elsevier B.V.

International Preliminary Report on Patentability issued for PCT Patent Application No. PCT/JP2017/033753 dated Mar. 24, 2020, 11 pages.

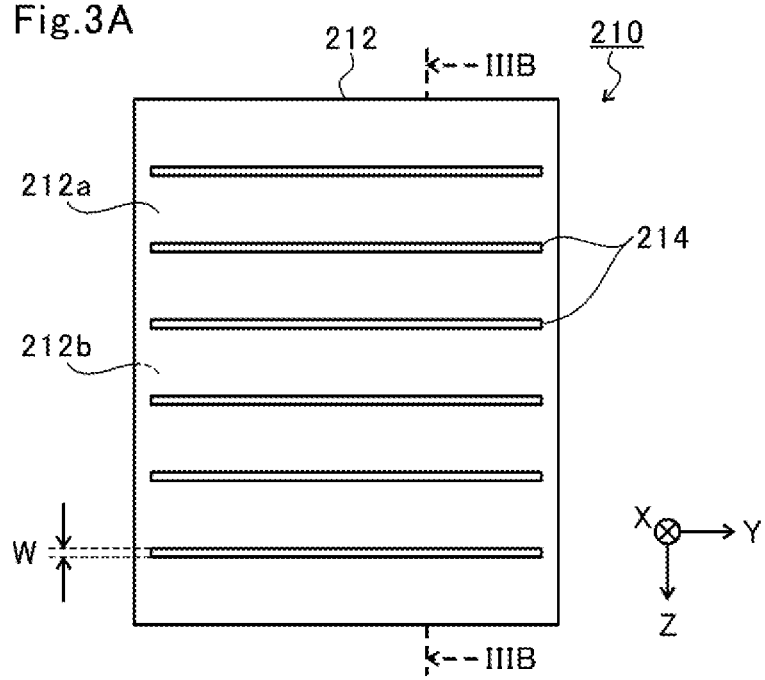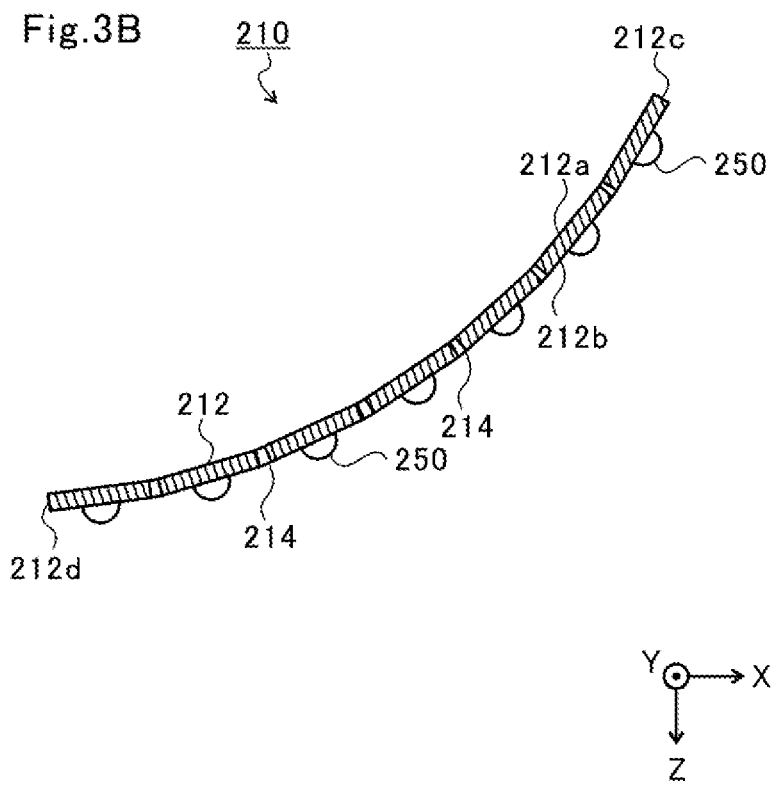

CULTURE DEVICE

CROSS REFERENCE TO RELATED APPLICATIONS

This application is a continuation application of International Application No. PCT/JP2017/033753, filed on Sep. 19, 2017, the entire contents of which are incorporated by reference herein.

BACKGROUND ART

Technical Field

The present disclosure relates to a culture device.

Related Art

In recent years, algae (in particular, microalgae) that can produce a biofuel (hydrocarbon or bio-diesel), a physiologically active substance, or the like have attracted attention. Investigations have been made on extracting a fuel, a physiologically active substance, or the like from such algae, or utilizing the algae themselves for a food, a drug, a cosmetic, or the like.

In order to extract a fuel or the like from the algae, or to utilize the algae themselves for a food or the like, the algae need to be mass-cultured with a culture device. As the culture device for mass-culturing the algae, for example, in Patent Literature 1, there is a disclosure of a raceway-type culture device. The raceway-type culture device is also called an open pond-type culture device or an outdoor pond-type culture device. The raceway-type culture device is an open-system reactor in which a liquid surface of a culture solution is exposed to the atmosphere. The algae that have been cultured in the culture solution in the culture device are separated from the culture solution, and then subjected to predetermined treatment and processed into a fuel, a food, or the like.

CITATION LIST

Patent Literature

Patent Literature 1: Japanese Patent Application Laid-Open No. 2011-239746

SUMMARY

Technical Problem

Incidentally, contamination (inclusion of germs) may occur in a culture solution during culture. In particular, the above-mentioned open-system reactor has a high probability of the inclusion of germs. Accordingly, the culture solution from which an object, such as algae, has been separated is discarded, and the culture device is supplied with a fresh culture solution. As described above, when the object is mass-cultured, there is a problem in that a large amount of the culture solution is discarded, resulting in an increase in culture cost. Therefore, there is a demand for the development of a technology capable of culturing an object at low cost.

In view of such problem, an object of the present disclosure is to provide a culture device capable of culturing an object at low cost.

Solution to Problem

In order to achieve the above-mentioned object, according to one aspect of the present disclosure, there is provided a culture device, including: a culture tank configured to store an object liquid that is a culture solution having suspended therein an object; a screen made of a metal, the screen including a main body and a plurality of through holes passing through the main body from a front surface thereof to a back surface thereof; a spray portion configured to spray the object liquid stored in the culture tank onto the front surface of the main body; an accommodation portion surrounding the back surface of the main body and configured to accommodate the culture solution having passed through the through holes; a UV light irradiation portion arranged in the accommodation portion and configured to radiate UV light; and a return portion configured to return the culture solution in the accommodation portion to the culture tank.

In addition, the accommodation portion may have, arranged in an inner lower part thereof, a liquid storage portion configured to store the culture solution, the UV light irradiation portion may be arranged in the liquid storage portion, and the return portion may be configured to return the culture solution stored in the liquid storage portion.

In addition, the accommodation portion may have, arranged in an inner lower part thereof, a liquid storage portion configured to store the culture solution, the accommodation portion may have arranged therein a guide plate configured to guide the culture solution having passed through the through holes into the liquid storage portion, the UV light irradiation portion may be arranged on the guide plate, and the return portion may be configured to return the culture solution stored in the liquid storage portion.

In addition, the UV light irradiation portion may be arranged on the back surface of the main body.

In addition, the culture device may further include: a turbidity measurement portion configured to measure a turbidity of the culture solution having passed through the through holes; and an irradiation control portion configured to control the UV light irradiation portion on the basis of the measured turbidity.

In addition, the UV light irradiation portion may be configured to radiate UV light with power generated by a power generation device configured to generate power using sunlight as an energy source.

In addition, the culture device may further include an oxidation promoter supply portion configured to supply an oxidation promoter to the accommodation portion.

In addition, the culture solution may contain a plurality of culture components serving as substances required for culture of the object, and the culture device may further include: a plurality of storage portions configured to respectively store a plurality of component solutions containing the culture components different from each other; a concentration measurement portion configured to measure a concentration of each of the plurality of culture components contained in the culture solution in the accommodation portion; and a supply portion configured to supply the component solutions from the plurality of storage portions to the culture solution in the accommodation portion, or to the culture solution to be returned from the accommodation portion to the culture tank, on the basis of the concentration of each of the culture components.

In addition, the culture device may further include a water storage portion configured to store water, wherein the supply portion is configured to supply water from the water storage portion to the culture solution on the basis of the concentration of each of the culture components.

In addition, the plurality of storage portions may include: any one or both of a phosphoric acid storage portion configured to store a component solution containing phosphoric acid as one of the culture components, and a sulfuric acid storage portion configured to store a component solution containing sulfuric acid as one of the culture components; and any one or both of a calcium storage portion configured to store a component solution containing calcium as one of the culture components, and an iron storage portion configured to store a component solution containing iron as one of the culture components.

Effects of Disclosure

According to the present disclosure, the object can be cultured at low cost.

BRIEF DESCRIPTION OF DRAWINGS

FIG. 3A is a plan view of a screen.
FIG. 3B is a cross-sectional view taken along the line IIIB-IIIB of FIG. 3A.

DESCRIPTION OF EMBODIMENTS

Now, with reference to the attached drawings, an embodiment of the present disclosure is described in detail. The dimensions, materials, and other specific numerical values represented in the embodiment are merely examples used for facilitating understanding, and do not limit the present disclosure unless otherwise stated. Elements having substantially the same functions and configurations in Description and Drawings are denoted by the same reference symbols to omit redundant description thereof. Further, illustration of elements with no direct relationship to the present disclosure is omitted.

[Culture Device 100]

In this embodiment, a culture device 100 configured to culture an object in a culture solution is described. A description is made by taking microalgae (algae), such as *Botryococcus braunii* or spirulina, as an example of the object. In addition, the algae may be a wild-type strain, or may be a mutant strain having an enlarged particle size as a result of genetic modification or mutation induction.

Figure 1:
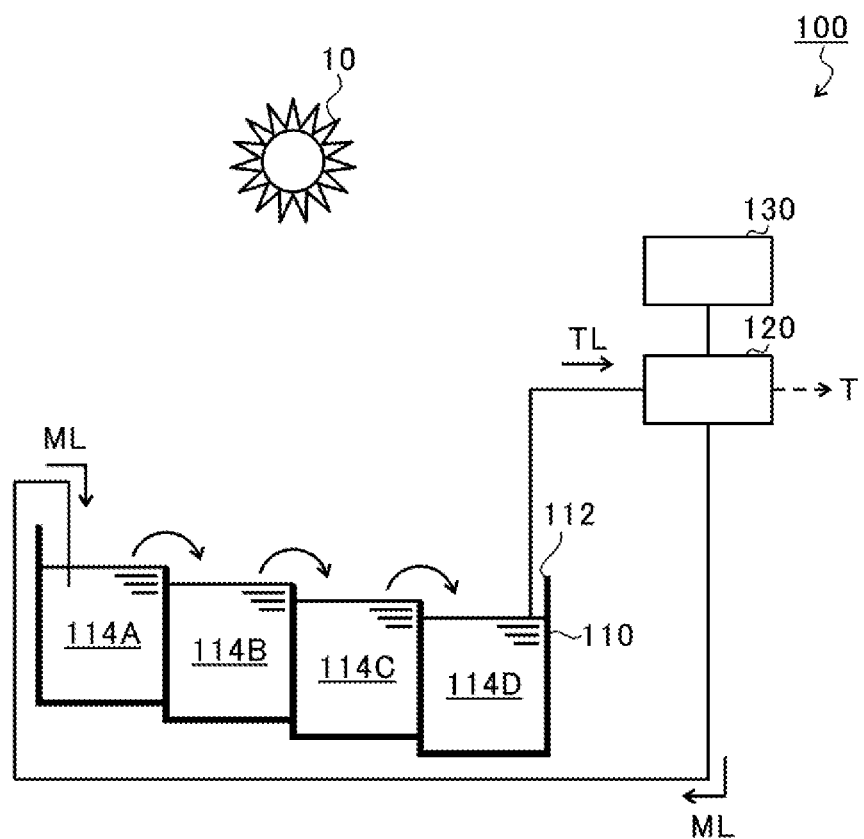
FIG. 1 is an explanatory view of a culture device.

FIG. 1 is an explanatory view of the culture device 100 according to this embodiment. As illustrated in FIG. 1, the culture device 100 includes a culture tank 110, a separation and regeneration unit 120, and a power generation device 130. In FIG. 1, the flow of a liquid is represented by an arrow. In addition, in FIG. 1, the culture solution is represented by ML, an object liquid is represented by TL, and the object is represented by T.

The culture tank 110 has an opening 112 on the upper surface thereof. The culture tank 110 is configured to store the object liquid. The object liquid is a culture solution having suspended therein the object. In addition, the object liquid is irradiated with sunlight 10 from the opening 112, and thus the object is cultured (grown) in the culture tank 110. In this embodiment, the culture tank 110 is divided into a plurality of divided regions 114 (denoted by 114A to 114D in FIG. 1) arranged in a row in a horizontal direction. The culture tank 110 is configured such that the divided regions 114 have water surfaces gradually descending in the order of the divided regions 114A, 114B, 114C, and 114D.

As described in detail later, the separation and regeneration unit 120 draws the object liquid from the culture tank 110. Then, the separation and regeneration unit 120 separates the drawn object liquid into the object and a post-culture solution. Subsequently, the separation and regeneration unit 120 regenerates the separated post-culture solution as a culture solution and returns the culture solution to the culture tank 110. In this embodiment, the separation and regeneration unit 120 draws the object liquid from the divided region 114D formed on one end side in the culture tank 110. In addition, the separation and regeneration unit 120 returns the regenerated culture solution to the divided region 114A formed on the other end side in the culture tank 110. Therefore, in the culture tank 110, the culture solution (object liquid) moves from the divided region 114A, to the divided region 114B, to the divided region 114C, and to the divided region 114D in the stated order.

The separation and regeneration unit 120 is configured to draw the object liquid from the divided region 114D, and to return the culture solution to the divided region 114A arranged at the farthest position from the divided region 114D. Consequently, the regenerated culture solution can have a long residence time in the culture tank 110. That is, a situation in which the regenerated culture solution is introduced into the separation and regeneration unit 120 through a shortcut (in a short residence time) can be avoided. Therefore, the separation and regeneration unit 120 can improve the regeneration efficiency of the culture solution.

In addition, part of the object separated by the separation and regeneration unit 120 is returned to the culture tank 110 together with the regenerated culture solution. The rest of the object separated by the separation and regeneration unit 120 is subjected to predetermined treatment and processed into a fuel, a food, or the like.

The power generation device 130 is configured to generate power using the sunlight 10 as an energy source. The power generation device 130 supplies the generated power to the separation and regeneration unit 120.

Thus, in the culture device 100 according to this embodiment, the culture solution used in the culture tank 110 is regenerated and returned to the culture tank 110. Consequently, the culture device 100 can reduce cost required for the culture solution, and hence can culture the object at low cost. Now, a specific configuration of the separation and regeneration unit 120 configured to regenerate the culture solution is described.

Figure 2:
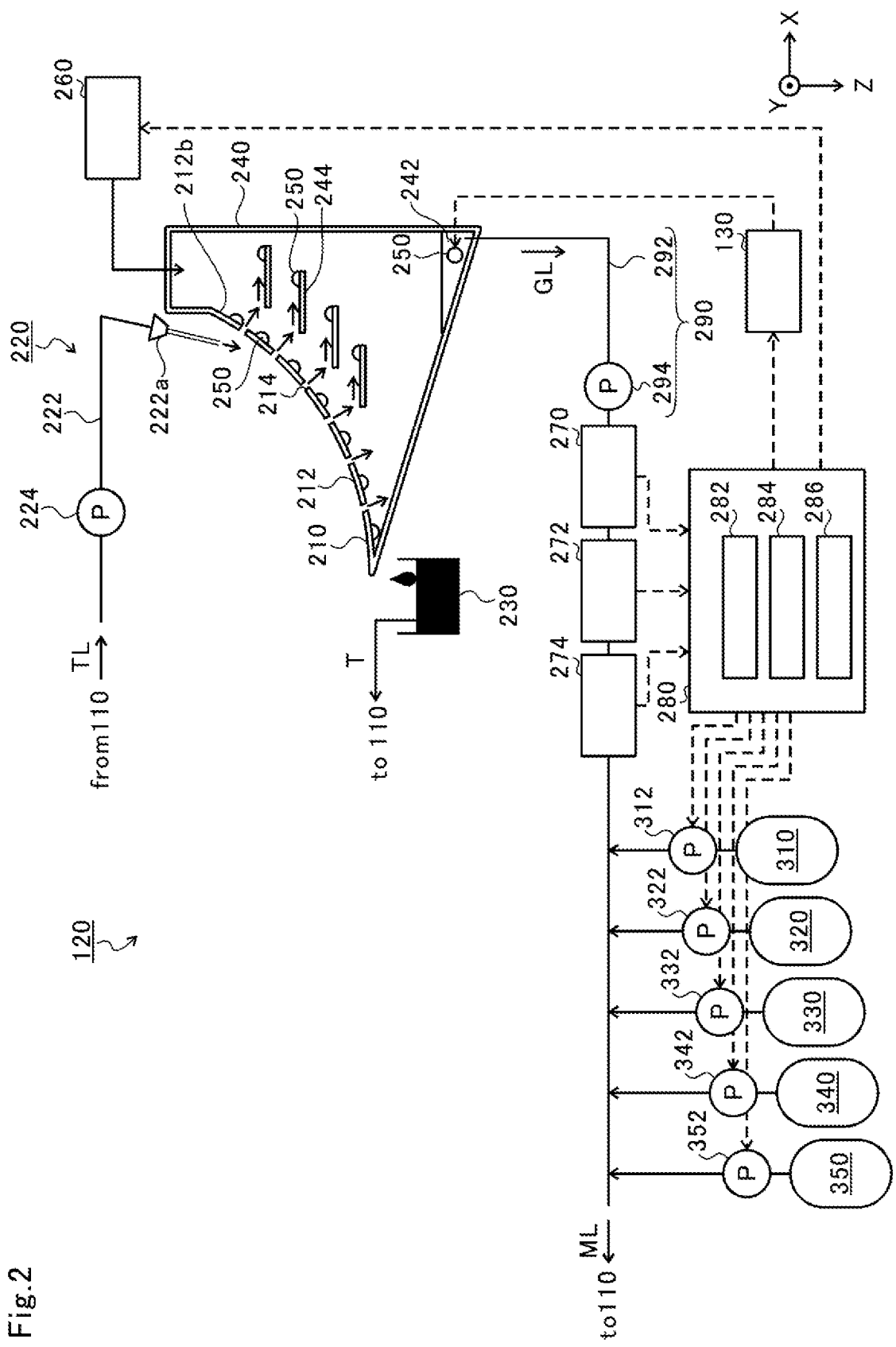
FIG. 2 is an explanatory view of a separation and regeneration unit.

FIG. 2 is an explanatory view of the separation and regeneration unit 120. In this embodiment, in the following figures including FIG. 2, an X-axis (horizontal direction), a Y-axis (horizontal direction), and a Z-axis (vertical direction) perpendicularly intersecting with each other are defined as illustrated in the figures. In addition, in FIG. 2, the flow of a substance, such as the object liquid, the post-culture solution, the culture solution, a component solution, the object, or an oxidation promoter, is represented by a solid-line arrow, and the flow of a signal is represented by a broken-line arrow. In addition, in FIG. 2, the culture solution is represented by ML, the post-culture solution is represented by GL, the object liquid is represented by TL, and the object is represented by T.

As illustrated in FIG. 2, the separation and regeneration unit 120 includes a screen 210, a spray portion 220, an object recovery tank 230, an accommodation portion 240, guide plates 244, UV light irradiation portions 250, an oxidation promoter supply portion 260, a turbidity measurement portion 270, an oxidation measurement portion 272, a concentration measurement portion 274, a central control portion 280, a return portion 290, a phosphoric acid storage portion 310 (storage portion), a first pump 312 (supply portion), a sulfuric acid storage portion 320 (storage portion), a second pump 322 (supply portion), a calcium storage portion 330 (storage portion), a third pump 332 (supply portion), an iron storage portion 340 (storage portion), a fourth pump 342 (supply portion), a water storage portion 350, and a fifth pump 352 (supply portion).

The screen 210 is configured to remove part of the post-culture solution from the object liquid. FIG. 3A is a plan view of the screen 210. FIG. 3B is a cross-sectional view taken along the line IIIB-IIIB of FIG. 3A. In FIG. 3A and FIG. 3B, slits 214 are illustrated larger than actual size to facilitate understanding.

As illustrated in FIG. 3A and FIG. 3B, the screen 210 includes a main body 212 and the slits (through holes) 214. The main body 212 is a plate-shaped member formed of a metal, such as stainless steel. As illustrated in FIG. 3B, the screen 210 is arranged so that one end side 212c of the main body 212 is vertically above another end side 212d (in the Z-axis direction in FIG. 3B).

The main body 212 is formed in a curved shape in which a front surface 212a side is concave. A plurality of the slits 214 are formed in the main body 212. The slits 214 pass through the main body 212 from the front surface 212a thereof to a back surface 212b thereof. The slits 214 extend in the Y-axis direction in each of FIG. 3A and FIG. 3B. In addition, a width W of each of the slits 214 in the Z-axis direction in FIG. 3A is smaller than the minimum particle size of the object. When the width of each of the slits 214 is set to be smaller than the minimum particle size of the object, a situation in which the object passes through the slits 214 can be avoided. Consequently, the screen 210 can prevent a reduction in recovery efficiency of the object. The minimum particle size of the object may be measured with an existing particle size measurement apparatus, such as a particle size distribution meter, and hence a detailed description is omitted herein. In addition, when the object forms colonies, the width of each of the slits 214 may be set to be smaller than the minimum particle size of the colonies.

Referring back to FIG. 2, the spray portion 220 is configured to suction the object liquid from the culture tank 110, and to spray the suctioned object liquid onto the screen 210. The spray portion 220 includes a pipe 222 and a pump 224. One end of the pipe 222 is immersed in the object liquid stored in the culture tank 110 (divided region 114D). The other end of the pipe 222 is connected to a nozzle 222a. The nozzle 222a has a tapered shape in which a path cross-sectional area thereof gradually decreases from a proximal end connected to the pipe 222 toward a distal end thereof. The pump 224 is arranged on the pipe 222.

Figure 4:
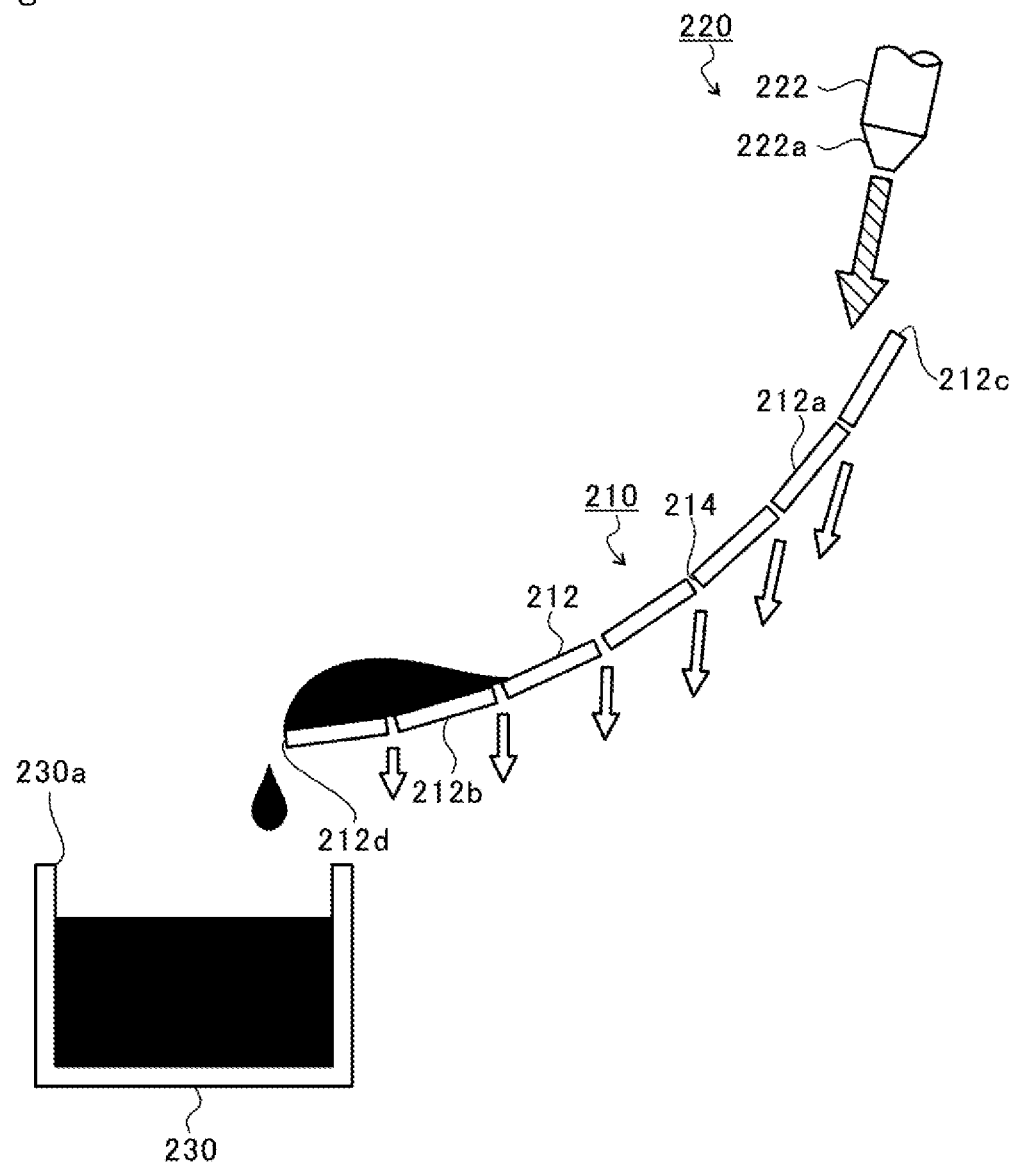
FIG. 4 is an explanatory view of a mode in which an object liquid is sprayed by a spray portion.

FIG. 4 is an explanatory view of a mode in which the object liquid is sprayed by the spray portion 220. In FIG. 4, the accommodation portion 240 and the UV light irradiation portions 250 are omitted to facilitate understanding. In FIG. 4, as indicated by a hatched arrow, the spray portion 220 sprays the object liquid toward the front surface 212a of the main body 212 of the screen 210. Then, part of the post-culture solution in the object liquid passes through the slits 214 to fall below the screen 210 (indicated by outlined arrows in FIG. 4). In addition, the object liquid from which part of the post-culture solution has been removed (filled in black in FIG. 4; hereinafter referred to as "concentrated object liquid") remains on the front surface 212a of the main body 212. When the spray portion 220 sprays the object liquid, the flow of the spray allows the object liquid to efficiently pass through the slits 214. Consequently, the dewatering efficiency of the object liquid (efficiency with which the post-culture solution is removed from the object liquid) can be improved.

In addition, in this embodiment, the spray portion 220 is configured to spray the object liquid in a direction intersecting with the surface direction of at least part of the front surface 212a of the main body 212. In other words, the spray portion 220 is configured to spray the object liquid in a direction intersecting with at least one normal line of the main body 212, the direction going from the one end side 212c toward the other end side 212d. Consequently, the impact of the spray causes the concentrated object liquid to move in the direction going from the one end side 212c toward the other end side 212d. Further, as described above, the main body 212 of the screen 210 is arranged so that the one end side 212c is vertically above the other end side 212d. Accordingly, the main body 212 allows the concentrated object liquid to move from the one end side 212c to the other end side 212d due to its own weight as well. Therefore, the culture device 100 does not require power dedicated to moving the concentrated object liquid, and hence can eliminate cost required for the power.

As described above, the concentrated object liquid moves from the one end side 212c to the other end side 212d, and in the course of the movement, the post-culture solution is further removed through the slits 214. Then, the concentrated object liquid that has reached the other end side 212d falls due to its own weight to be accommodated in the object recovery tank 230.

The object recovery tank 230 is configured to accommodate the concentrated object liquid. The object recovery tank 230 is arranged below the other end side 212d of the main body 212 so that an upper opening 230a faces the other end side 212d. Part of the concentrated object liquid accommodated in the object recovery tank 230 is returned to the culture tank 110. In addition, the rest of the concentrated object liquid accommodated in the object recovery tank 230 is delivered to a downstream treatment facility.

Referring back to FIG. 2, the accommodation portion 240 surrounds the back surface 212b of the main body 212 of the screen 210. The accommodation portion 240 is configured to accommodate the post-culture solution having passed through the slits 214 (culture solution separated by the screen 210).

The post-culture solution having passed through the slits 214 falls inside the accommodation portion 240 due to its own weight. Therefore, a liquid storage portion 242 configured to temporarily store the post-culture solution is formed in an inner lower part of the accommodation portion 240.

In addition, a plurality of the guide plates 244 are arranged in the accommodation portion 240. The guide plates 244 are configured to guide the post-culture solution having passed through the slits 214 into the liquid storage portion 242.

The UV light irradiation portions 250 are arranged in the accommodation portion 240. In this embodiment, the UV light irradiation portions 250 each include an LED. The UV light irradiation portions 250 are each configured to radiate UV light. The UV light irradiation portions 250 each radiate UV light having a wavelength having the strongest sterilization action (wavelength for destroying DNA, such as 253.7 nm).

In addition, in this embodiment, the UV light irradiation portions 250 are arranged on the back surface 212b of the main body 212, on the guide plates 244, and in the liquid storage portion 242. The sterilization effect of the UV light becomes higher as a distance from a light source (each of the UV light irradiation portions 250) becomes shorter, and as an irradiation time becomes longer. Therefore, when the residence time of the post-culture solution in the accommodation portion 240 (liquid storage portion 242) is increased, the sterilization effect can be enhanced, but a sterilization time is lengthened.

In view of the foregoing, the UV light irradiation portions 250 are arranged in the vicinity of a path through which the post-culture solution passes, i.e., on the back surface 212b of the main body 212, on the guide plates 244, and in the liquid storage portion 242. Consequently, the distance from the light source to the post-culture solution (germs) can be reduced. Therefore, the culture device 100 can shorten the sterilization time while enhancing the sterilization effect.

In addition, in this embodiment, the UV light irradiation portions 250 are each configured to radiate UV light with power generated by the power generation device 130. Germs are grown owing to the sunlight 10, and hence a period of time (e.g., daytime) during which the power generation efficiency of the power generation device 130 configured to generate power using the sunlight 10 as an energy source is high approximately coincides with a period of time in which the growth rate of the germs is high. Therefore, when the UV light irradiation portions 250 are driven (UV light is radiated) with the power generated by the power generation device 130, the UV light can be effectively radiated during the growth time of the germs, and hence sterilization can be efficiently performed.

The oxidation promoter supply portion 260 is configured to supply an oxidation promoter to the accommodation portion 240. The oxidation promoter to be supplied by the oxidation promoter supply portion 260 is, for example, ozone, hydrogen peroxide, or hypochlorous acid. Herein, a description is made by taking as an example a configuration in which the oxidation promoter supply portion 260 supplies ozone as the oxidation promoter.

In this embodiment, the oxidation promoter supply portion 260 is configured to supply ozone at least to the upstream side of the UV light irradiation portion 250 arranged in the liquid storage portion 242. When the oxidation promoter supply portion 260 supplies ozone, ozone can be dissolved in the post-culture solution. Therefore, UV light is radiated to the post-culture solution having dissolved therein ozone. Consequently, the culture device 100 can perform an advanced oxidation process (AOP), and hence can further improve the sterilization effect.

The turbidity measurement portion 270 is configured to measure the turbidity of the post-culture solution (sterilized post-culture solution) drawn from the accommodation portion 240 by the return portion 290 to be described later.

The oxidation measurement portion 272 is configured to measure the concentration of ozone (oxidation promoter) in the post-culture solution (sterilized post-culture solution) drawn from the accommodation portion 240 by the return portion 290.

The concentration measurement portion 274 is configured to measure the concentration of each of culture components contained in the post-culture solution (sterilized post-culture solution) drawn from the accommodation portion 240 by the return portion 290. The concentration measurement portion 274 measures the concentration using, for example, colorimetry. The culture components are substances essential to the culture of the object, and herein, a description is made by taking phosphoric acid, sulfuric acid, calcium, and iron as examples thereof. In addition, the post-culture solution used in the measurement by the concentration measurement portion 274 may be discarded. In addition, the post-culture solution used in the measurement by the concentration measurement portion 274 may be returned to a pipe 292 included in the return portion 290.

The central control portion 280 includes a semiconductor integrated circuit including a central processing unit (CPU). The central control portion 280 is configured to read out, for example, a program or parameters for operating the CPU itself from a ROM. The central control portion 280 is configured to manage and control the entire separation and regeneration unit 120 in cooperation with a RAM serving as a working area and other electronic circuits. In this embodiment, the central control portion 280 also functions as an irradiation control portion 282, an oxidation control portion 284, and a supply amount control portion 286 (supply portion).

The irradiation control portion 282 is configured to control the UV light irradiation portions 250 on the basis of the turbidity measured by the turbidity measurement portion 270. For example, when the turbidity is equal to or higher than a predetermined turbidity threshold value, the irradiation control portion 282 controls the UV light irradiation portions 250 so that the irradiation frequency (or irradiation output) of the UV light is increased as compared to that in a case in which the turbidity is lower than the turbidity threshold value.

When the number of germs in the post-culture solution is relatively large, the turbidity is increased. Accordingly, when the irradiation control portion 282 controls the UV light irradiation portions 250 on the basis of the turbidity, the amount of power consumption can be reduced while the sterilization efficiency is improved.

The oxidation control portion 284 is configured to control the oxidation promoter supply portion 260 on the basis of the concentration of ozone measured by the oxidation measurement portion 272. For example, when the concentration of ozone is equal to or higher than a predetermined concentration threshold value, the oxidation control portion 284 controls the oxidation promoter supply portion 260 so that the supply amount of ozone (oxidation promoter) is decreased as compared to that in a case in which the concentration of ozone is lower than the concentration threshold value.

When the concentration of ozone in the culture solution to be returned to the culture tank 110 is high, the culture (growth) of the object may be inhibited. Accordingly, when the oxidation control portion 284 controls the oxidation promoter supply portion 260 on the basis of the concentration of ozone, the inhibition of the culture of the object can be prevented while the sterilization efficiency is improved.

The supply amount control portion 286 is configured to supply component solutions from a plurality of storage portions to be described later to the post-culture solution on the basis of the concentration of each of the culture components measured by the concentration measurement portion 274. Control by the supply amount control portion 286 is described in detail later.

The return portion 290 includes the pipe 292 and a return pump 294. The return portion 290 is configured to suction the sterilized post-culture solution from the accommodation portion 240, and to return the sterilized post-culture solution to the culture tank 110. The pipe 292 is configured to connect the liquid storage portion 242 of the accommodation portion 240 to the culture tank 110 (divided region 114A). The return pump 294 is arranged on the pipe 292. In the pipe 292 on the downstream side of the return pump 294, an in-line mixer is arranged. The in-line mixer is configured to promote mixing between the component solutions supplied by the supply amount control portion 286, and the post-culture solution.

In this case, when the return portion 290 returns the sterilized post-culture solution as it is, the culture of the object may not be promoted in the culture tank 110. Specifically, the culture components contained in the culture solution are consumed by the object during culture. Accordingly, when the post-culture solution is returned as it is to the culture tank 110, the culture of the object is not promoted in the case where the culture components are deficient.

In view of the foregoing, in the culture device 100, the sterilized post-culture solution is supplied with culture components and then returned to the culture tank 110. Now, the supply of the culture components is specifically described.

The phosphoric acid storage portion 310 is configured to store a component solution containing a predetermined concentration of phosphoric acid (phosphate ion) (hereinafter referred to as "phosphoric acid solution") out of the culture components constituting the culture solution. The concentration of phosphoric acid in the phosphoric acid solution stored in the phosphoric acid storage portion 310 is stored in a memory (not shown). The first pump 312 is configured to supply the phosphoric acid solution stored in the phosphoric acid storage portion 310 to the downstream side of the concentration measurement portion 274 in the pipe 292 in accordance with control by the supply amount control portion 286.

The sulfuric acid storage portion 320 is configured to store a component solution containing a predetermined concentration of sulfuric acid (sulfate ion) (hereinafter referred to as "sulfuric acid solution") out of the culture components constituting the culture solution. The concentration of sulfuric acid in the sulfuric acid solution stored in the sulfuric acid storage portion 320 is stored in a memory (not shown). The second pump 322 is configured to supply the sulfuric acid solution stored in the sulfuric acid storage portion 320 to the downstream side of the concentration measurement portion 274 in the pipe 292 in accordance with control by the supply amount control portion 286.

The calcium storage portion 330 is configured to store a component solution containing a predetermined concentration of calcium (calcium ion) (hereinafter referred to as "calcium solution") out of the culture components constituting the culture solution. The concentration of calcium in the calcium solution stored in the calcium storage portion 330 is stored in a memory (not shown). The third pump 332 is configured to supply the calcium solution stored in the calcium storage portion 330 to the downstream side of the concentration measurement portion 274 in the pipe 292 in accordance with control by the supply amount control portion 286.

The iron storage portion 340 is configured to store a component solution containing a predetermined concentration of iron (iron ion) (hereinafter referred to as "iron solution") out of the culture components constituting the culture solution. The concentration of iron in the iron solution stored in the iron storage portion 340 is stored in a memory (not shown). The fourth pump 342 is configured to supply the iron solution stored in the iron storage portion 340 to the downstream side of the concentration measurement portion 274 in the pipe 292 in accordance with control by the supply amount control portion 286.

The water storage portion 350 is configured to store water. The fifth pump 352 is configured to supply the water stored in the water storage portion 350 to the downstream side of the concentration measurement portion 274 in the pipe 292 in accordance with control by the supply amount control portion 286.

The supply amount control portion 286 is configured to control the first pump 312, the second pump 322, the third pump 332, the fourth pump 342, and the fifth pump 352 on the basis of the concentration of each of the culture components measured by the concentration measurement portion 274.

For example, when the concentration of phosphoric acid measured by the concentration measurement portion 274 is below a predetermined proper range, the supply amount control portion 286 drives the first pump 312 on the basis of the concentration of the phosphoric acid solution stored in the memory to supply the phosphoric acid solution in a predetermined amount (or for a predetermined period of time based on the flow rate of the first pump 312) until the concentration of phosphoric acid falls within the proper range. In the same manner, when the concentration of sulfuric acid measured by the concentration measurement portion 274 is below a predetermined proper range, the supply amount control portion 286 drives the second pump 322 on the basis of the concentration of the sulfuric acid solution stored in the memory to supply the sulfuric acid solution in a predetermined amount (or for a predetermined period of time based on the flow rate of the second pump 322) until the concentration of sulfuric acid falls within the proper range. When the concentration of calcium measured by the concentration measurement portion 274 is below a predetermined proper range, the supply amount control portion 286 drives the third pump 332 on the basis of the concentration of the calcium solution stored in the memory to supply the calcium solution in a predetermined amount (or for a predetermined period of time based on the flow rate of the third pump 332) until the concentration of calcium falls within the proper range. When the concentration of iron measured by the concentration measurement portion 274 is below a predetermined proper range, the supply amount control portion 286 drives the fourth pump 342 on the basis of the concentration of the iron solution stored in the memory to supply the iron solution in a predetermined amount (or for a predetermined period of time based on the flow rate of the fourth pump 342) until the concentration of iron falls within the proper range.

In addition, when the concentration of one or a plurality of culture components out of the culture components measured by the concentration measurement portion 274 exceeds the predetermined proper range, the supply amount control portion 286 drives the fifth pump 352 to supply water. Specifically, the supply amount control portion 286 drives the fifth pump 352 until the concentration of the culture components that has the largest difference from the proper range falls within the proper range. Then, the supply amount control portion 286 estimates the current concentrations (concentrations after water addition) of the other culture components on the basis of the concentrations of the other culture components measured by the concentration measurement portion 274, and the amount of water supplied from the water storage portion 350. Subsequently, the supply amount control portion 286 controls the first pump 312, the second pump 322, the third pump 332, and the fourth pump 342 so that the other culture components fall within the proper ranges on the basis of the estimated current concentrations of the other culture components.

Thus, the post-culture solution having the culture components within the proper ranges (regenerated culture solution) is returned to the culture tank 110 by the return portion 290.

As described above, in the culture device 100 according to this embodiment, the separation and regeneration unit 120 is configured to sterilize the culture solution used in the culture tank 110, and to return the sterilized culture solution to the culture tank 110. In addition, when the culture device 100 includes the plurality of storage portions (phosphoric acid storage portion 310, sulfuric acid storage portion 320, calcium storage portion 330, and iron storage portion 340) and the supply amount control portion 286, the concentrations of all the culture components in the post-culture solution to which the component solutions have been added can be caused to fall within the proper ranges. Consequently, the culture device 100 can reuse the used culture solution. Therefore, cost required for the culture solution can be reduced, and hence the object can be cultured at low cost.

In addition, in the culture device 100 according to this embodiment, the component solutions different from each other are respectively stored in the plurality of storage portions. For example, when the phosphoric acid solution and the calcium solution are stored in one storage portion, deposition of calcium phosphate occurs. In addition, when the phosphoric acid solution and the iron solution are stored in one storage portion, deposition of iron phosphate occurs. In addition, when the sulfuric acid solution and the calcium solution are stored in one storage portion, deposition of calcium sulfate occurs. In that case, a problem arises in that the concentrations of the culture components in the component solutions fluctuate, or in that the supply port of the storage portion is clogged by the deposition. In view of this, with the configuration in which the different component solutions are respectively stored in the plurality of storage portions, the culture device 100 can avoid the problem that the culture components in the component solutions cause together.

In addition, the concentration measurement portion 274 is configured to measure the concentration of each of the plurality of culture components contained in the post-culture solution after the object has been separated therefrom by the screen 210. Consequently, measurement accuracy can be improved as compared to that in a case in which the object liquid (post-culture solution before the object has been separated therefrom) is subjected to measurement as it is.

In addition, by virtue of the configuration in which the culture device 100 includes the UV light irradiation portions 250, a situation in which the culture components are consumed by germs can be avoided.

The embodiment has been described above with reference to the attached drawings, but, needless to say, the present disclosure is not limited to the embodiment. It is apparent that those skilled in the art could arrive at various alternations and modifications within the scope of claims, and those examples are construed as naturally falling within the technical scope.

For example, in the above-mentioned embodiment, a description has been made by taking microalgae as an example of the object to be cultured in the culture device 100. However, the object is not limited, and may be, for example, algae other than microalgae, or microorganisms or cells other than algae.

In addition, in the above-mentioned embodiment, a description has been made by taking as an example a case in which the screen 210 is formed of stainless steel. However, as long as the screen is made of a metal, the kind of the metal is not limited. In addition, the front surface of the screen may be coated to prevent the corrosion of the main body 212.

In addition, in the above-mentioned embodiment, a description has been made by taking the slits 214, each of which has a rectangular shape, as an example of the through holes to be formed in the main body 212. However, the shape of each of the through holes is not limited. In addition, the size of each of the through holes is desirably smaller than the minimum particle size of the object (or colonies), but the size of at least one of the through holes only needs to be smaller than the minimum particle size of the object.

In addition, in the above-mentioned embodiment, a description has been made by taking as an example a case in which the widths of all the slits 214 are smaller than the minimum particle size of the object. However, the width of at least one of the slits 214 only needs to be smaller than the minimum particle size of the object.

In addition, in the above-mentioned embodiment, a description has been made by taking as an example the main body 212 having a curved shape in which the front surface 212a side is concave. However, the shape of the main body 212 is not limited.

In addition, in the above-mentioned embodiment, a description has been made by taking as an example a configuration in which the UV light irradiation portions 250 are arranged on the back surface 212b of the main body 212, in the liquid storage portion 242, and on the guide plates 244. However, the UV light irradiation portion 250 may be arranged at any one site out of the back surface 212b of the main body 212, the liquid storage portion 242, and the guide plates 244. When the UV light irradiation portion 250 is arranged on the back surface 212b of the main body 212, the UV light irradiation portion 250 can radiate UV light to all the culture solution that passes through the slits 214. When the UV light irradiation portion 250 is arranged in the liquid storage portion 242, the UV light irradiation portion 250 can radiate UV light to all the culture solution to be returned by the return portion 290. In addition, the culture solution is to be exposed to the UV light during a period of being stored in the liquid storage portion 242, and hence the sterilization efficiency can be improved. When the UV light irradiation portions 250 are arranged on the guide plates 244, the UV light irradiation portions 250 can radiate UV light to all the culture solution that has passed through the slits 214 and is to be guided into the liquid storage portion 242. In addition, the UV light irradiation portion 250 only needs to be able to irradiate the culture solution with UV light, and the position at which the UV light irradiation portion 250 is arranged is not limited as long as the position is in the accommodation portion 240.

In addition, in the above-mentioned embodiment, a description has been made by taking as an example a configuration in which the UV light irradiation portions 250 each radiate UV light with power generated by the power generation device 130. However, the power supply source for the UV light irradiation portions 250 is not limited to the power generation device 130, and may be a commercial power supply.

In addition, in the above-mentioned embodiment, a description has been made by taking as an example a configuration in which the wavelength of the UV light radiated by each of the UV light irradiation portions 250 is 253.7 nm. However, the UV light irradiation portions 250 only need to be capable of radiating UV light for sterilizing the culture solution, and the wavelength of the UV light is not limited. For example, UV light in a predetermined wavelength range including 253.7 nm may be radiated.

In addition, in the above-mentioned embodiment, a description has been made by taking as an example a case in which the UV light irradiation portions 250 each include an LED. However, the UV light irradiation portions 250 may each include a UV sterilization lamp (mercury lamp).

In addition, in the above-mentioned embodiment, a description has been made by taking the phosphoric acid storage portion 310, the sulfuric acid storage portion 320, the calcium storage portion 330, and the iron storage portion 340 as examples of the storage portions. However, a storage portion configured to store a component solution containing a culture component other than phosphoric acid, sulfuric acid, calcium, and iron may be arranged. In addition, culture components that do not cause a problem (e.g., deposition) even when allowed to coexist with each other may be stored together in one storage portion.

In addition, in the above-mentioned embodiment, a description has been made by taking the screen 210 and the spray portion 220 as an example of a separation mechanism configured to draw the object liquid from the culture tank 110, and to separate the object liquid into the object and the post-culture solution. However, the separation mechanism is not limited. The separation mechanism may include, for example, a pump configured to draw the object liquid from the culture tank, and a filter configured to filter the drawn object liquid. In addition, a centrifuge or a hydrocyclone may be adopted in place of the filter in the separation mechanism.

In addition, the central control portion 280 may be configured to adjust the amount of the concentrated object liquid to be returned from the object recovery tank 230 to the culture tank 110 on the basis of the turbidity measured by the turbidity measurement portion 270. With this, the concentration of the object in the culture tank 110 can be maintained within a proper range.

INDUSTRIAL APPLICABILITY

The present disclosure can be utilized in a culture device.

REFERENCE SIGNS LIST

100 culture device
110 culture tank
130 power generation device
210 screen
212 main body
212a front surface
212b back surface
214 slit (through hole)
220 spray portion
240 accommodation portion
242 liquid storage portion
244 guide plate
250 UV light irradiation portion
260 oxidation promoter supply portion
270 turbidity measurement portion
272 oxidation measurement portion
274 concentration measurement portion
282 irradiation control portion
286 supply amount control portion (supply portion)
290 return portion
310 phosphoric acid storage portion (storage portion)
312 first pump (supply portion)
320 sulfuric acid storage portion (storage portion)
322 second pump (supply portion)
330 calcium storage portion
332 third pump (supply portion)
340 iron storage portion (storage portion)
342 fourth pump (supply portion)
350 water storage portion
352 fifth pump (supply portion)

What is claimed is:

1. A culture device, comprising:
   a culture tank configured to store an object liquid that is a culture solution having suspended therein an object;
   a screen made of a metal, the screen including a main body and a plurality of through holes passing through the main body from a front surface thereof to a back surface thereof;
   a spray portion comprising a pipe and a pump, wherein one end of the pipe is immersed in the object liquid stored in the culture tank,
   the pump is arranged on the pipe, and
   the spray portion is configured to spray the object liquid stored in the culture tank onto the front surface of the main body;
   an accommodation portion surrounding the back surface of the main body and configured to accommodate the culture solution having passed through the through holes;
   a liquid storage portion arranged in an inner lower part of the accommodation portion and configured to store the culture solution;
   a guide plate arranged in the accommodation portion and configured to guide the culture solution having passed through the through holes into the liquid storage portion;
   at least one UV light irradiation portion comprising one or both of an LED and a mercury lamp, wherein the at least one UV light irradiation portion is arranged at least on the guide plate and configured to radiate UV light; and
   a return portion configured to return the culture solution in the accommodation portion to the culture tank.

2. The culture device according to claim 1, wherein
   the at least one UV light irradiation portion includes an additional UV light irradiation portion that is arranged on the back surface of the main body, and
   the additional UV light irradiation portion comprises one or both of an LED and a mercury lamp.

3. The culture device according to claim 1, further comprising:
   a turbidimeter configured to measure a turbidity of the culture solution having passed through the through holes; and
   an irradiation control portion comprising a central processing unit (CPU), wherein the irradiation control portion is configured to control the at least one UV light irradiation portion on the basis of the measured turbidity.

4. The culture device according to claim 1, wherein the at least one UV light irradiation portion is configured to radiate UV light with power generated by a power generator configured to generate power using sunlight as an energy source.

5. The culture device according to claim 1, further comprising an oxidation promoter feeder configured to supply an oxidation promoter to the accommodation portion.

6. The culture device according to claim 1,
   wherein the culture solution contains a plurality of culture components serving as substances required for culture of the object, and wherein the culture device further comprises:
- a plurality of storage portions configured to respectively store a plurality of component solutions containing the culture components different from each other;
- a concentration measurement portion configured to measure a concentration of each of the plurality of culture components contained in the culture solution in the accommodation portion using colorimetry; and
- a supply portion comprising pumps connected to each of the plurality of storage portions, wherein the supply portion is configured to supply the component solutions from the plurality of storage portions to the culture solution in the accommodation portion, or to the culture solution to be returned from the accommodation portion to the culture tank, on the basis of the concentration of each of the culture components.

7. The culture device according to claim 6, further comprising a water storage portion configured to store water, wherein the supply portion further comprises an additional pump connected to the water storage portion and is configured to supply water from the water storage portion to the culture solution on the basis of the concentration of each of the culture components.

8. The culture device according to claim 6, wherein the plurality of storage portions include:
- any one or both of a phosphoric acid storage portion configured to store a component solution containing phosphoric acid as one of the culture components, and a sulfuric acid storage portion configured to store a component solution containing sulfuric acid as one of the culture components; and
- any one or both of a calcium storage portion configured to store a component solution containing calcium as one of the culture components, and an iron storage portion configured to store a component solution containing iron as one of the culture components.

\* \* \* \* \*